US00PP24010P3

(12) United States Plant Patent
Suphachadiwong

(10) Patent No.: US PP24,010 P3
(45) Date of Patent: Oct. 29, 2013

(54) ***DRACAENA REFLEXA* PLANT NAMED 'IDEA1010'**

(50) Latin Name: *Dracaena reflexa*
Varietal Denomination: IDEA1010

(75) Inventor: Meechai Suphachadiwong, Bangkok (TH)

(73) Assignee: Plants and Ideas (TH)

( * ) Notice: Subject to any disclaimer, the term of this patent is extended or adjusted under 35 U.S.C. 154(b) by 73 days.

(21) Appl. No.: 13/374,449

(22) Filed: Dec. 28, 2011

(65) Prior Publication Data

US 2012/0174272 P1 Jul. 5, 2012

(30) Foreign Application Priority Data

Dec. 29, 2010 (QZ) ..... PBR 20102900

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — Cassandra Bright

(57) ABSTRACT

A new and distinct *Dracaena reflexa* cultivar named 'IDEA1010' is disclosed, characterized by variegated, long, thin foliage. The new variety is a *Dracaena reflexa,* normally produced as an ornamental plant

1 Drawing Sheet

Latin name of the genus and species: *Dracaena reflexa.*
Variety denomination: 'IDEA1010'.

BACKGROUND OF THE INVENTION

The new *Dracaena reflexa* cultivar is a product of a chance discovery by the inventor, Meechai Suphachaiwong, in Bangkok, Thailand. The inventor identified and selected the mutated plant with interesting variegation and proceeded to test its suitability for ornamental commercial applications. Inventor claims foreign priority to a previously filed EU application 2010/2900 filed Dec. 29, 2010, grant pending.

The parent is an unpatented, unnamed variety of *Dracaena reflexa.* The new variety was discovered in June 2009, by the inventor as a naturally occurring whole plant mutation, in a commercial greenhouse in Bangkok, Thailand.

Asexual reproduction of the new cultivar 'IDEA1010' by vegetative cuttings was first performed at a commercial greenhouse in Bangkok, Thailand during the Fall of 2009 and has shown that the unique features of this cultivar are stable and reproduced true to type in successive generations. Plants of the new variety have not been sold at the time of filing this application.

SUMMARY OF THE INVENTION

The cultivar 'IDEA1010' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IDEA1010' These characteristics in combination distinguish 'IDEA1010' as a new and distinct *Dracaena reflexa* cultivar:

1. Unique variegated foliage.
2. Long, narrow foliage.

Plants of the new cultivar 'IDEA1010' are similar to plants of the parent, *Dracaena reflexa* in most horticultural characteristics, however, plants of the new cultivar 'IDEA1010' produce variegated leaves compared to the solid green foliage of the parent.

Commercial Comparison

Plants of 'IDEA1010' are best compared to the parent variety.

BRIEF DESCRIPTION OF THE PHOTOGRAPHS

The accompanying photograph in FIG. 1 illustrates in full color a typical plant of 'IDEA1010' grown in a greenhouse, in a 12 cm pot.

Age of the plant photographed is approximately 2 months from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'IDEA1010' plants grown in a greenhouse, in Honselersdijk, The Netherlands. The growing temperature ranged from 25° to 36° C. during the day to 17° to 25° C. during the night. General light conditions are normal sunlight. Measurements and numerical values represent averages of typical plant types. Plants are approximately 2 months old from a rooted cutting.

Botanical classification: *Dracaena reflexa* 'IDEA1010'.

PROPAGATION

Time to initiate roots: About 6 weeks at approximately 25° to 28° C.

Root description: Moderately thick, moderately fibrous, not fleshy, young roots near RHS White 155A, older roots Greyed-Orange 163C.

Time to produce rooted plantlet: Approximately 4-5 weeks at approximately 22 ° C.

PLANT

Growth habit: Upright and outwardly arching.

Height: Approximately 25.4 cm.

Plant spread: Approximately 34.3 cm.

Growth rate: Moderate, approximately 8 cm per month.

Branching characteristics: One main stem. Will only develop lateral branches after pinching/pruning.

Diameter of stem: Approximately 0.5 cm.

Texture of stem: Smooth, dull.

Color of stem: Near RHS Yellow-Green 152D.

Stem strength: Very strong.

Number of leaves per stem: Average 31.

Internode length: Average 0.4 cm.

Age of plant described: Approximately 2 months.

FOLIAGE

Leaf:

*Arrangement.*—Alternate (spirally).

*Average length.*—Approximately 19.7 cm.

*Average width.*—Approximately 1.4 cm.

*Shape of blade.*—Lorate.

*Aspect.*—Slightly curved downward.

*Apex.*—Long acuminate, not sharp.

*Base.*—Broad cuneate.

*Attachment.*—Sheathing.

*Margin.*—Entire.

*Texture of top surface.*—Smooth, moderately glossy.

*Texture of bottom surface.*—Smooth, moderately glossy.

*Color.*—Young foliage upper side: Near RHS 137B, margin and striping Yellow-Green 154B and 154C. Young foliage under side: Near RHS 137B, margin and striping Yellow-Green 151 D. Mature foliage upper side: Near RHS N137B margin and striping Yellow-Green 154D, greener towards the base: 144B. Mature foliage under side: Near RHS 137B margin and striping Yellow-Green 154D, greener towards the base: 144B and 145A.

Venation:

*Type.*—Parallel.

*Venation coloration upper side.*—Indistinguishable from leaf blade.

*Venation coloration under side.*—Indistinguishable from leaf blade.

Sheath:

*Average length.*—Approximately 0.3 cm.

*Average width.*—Approximately 0.6 cm.

*Color.*—Central section near RHS Yellow-Green 144A margins near 154B and 154C.

*Texture.*—Smooth, moderately glossy.

Other structures: None present.

FLOWER

Typically non flowering: No flowers, no reproductive organs observed.

OTHER CHARACTERISTICS

Seed production: Not observed to date.

Disease resistance: Neither resistance nor susceptibility to diseases or pests has been observed in this variety.

Temperature tolerance: Low temperature tolerance to at least 5° C., high temperatures to at least 40° C.

Drought tolerance: Moderate tolerance for drought.

What is claimed is:

1. A new and distinct cultivar of *Dracaena reflexa* plant named 'IDEA1010' as herein illustrated and described.

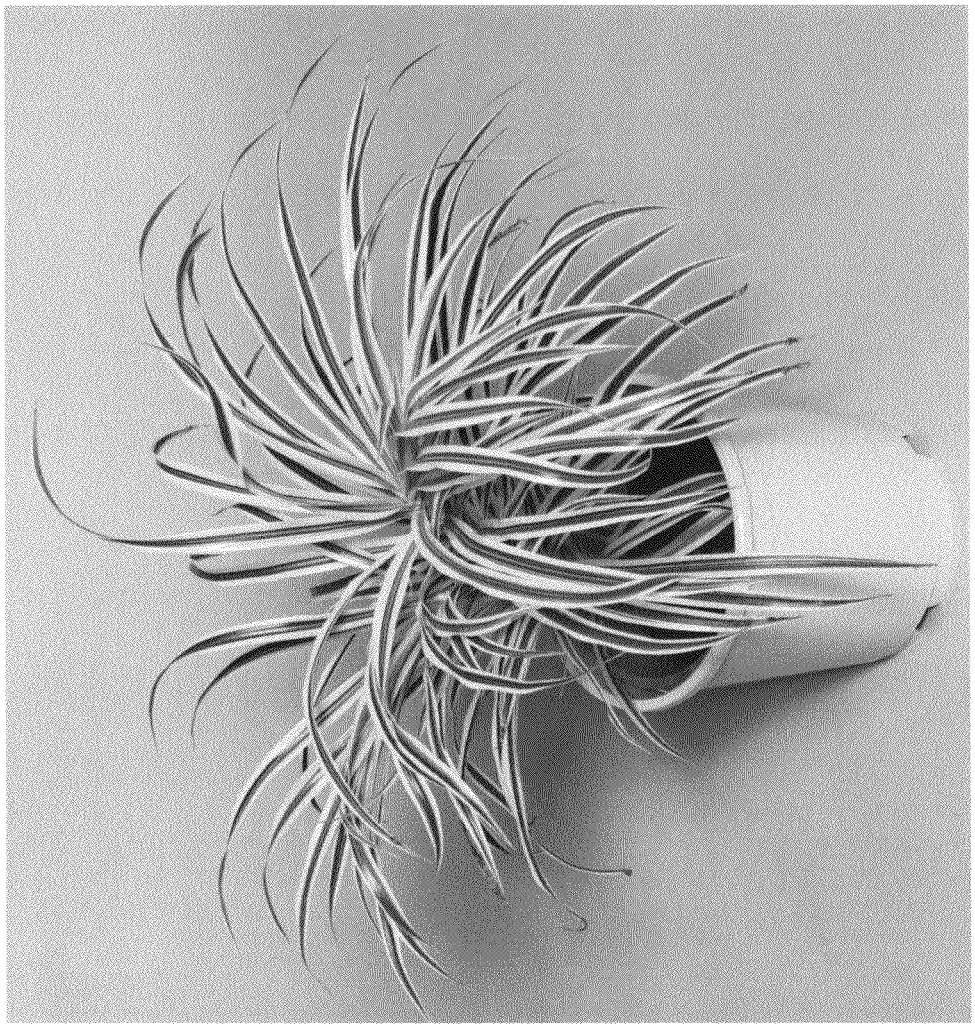

* * * * *